US012745994B2

(12) United States Patent
Isilki et al.

(10) Patent No.: US 12,745,994 B2
(45) Date of Patent: Sep. 29, 2026

(54) OCCLUDER WITH STRETCHABLE WAIST

(71) Applicant: Occlutech GmbH, Jena (DE)

(72) Inventors: Cansel Isilki, Schaffhausen (CH); Secil Soyutemiz, Schaffhausen (CH); Olcay Cavusoglu, Schaffhausen (CH); Gareth Morgan, Schaffhausen (CH)

(73) Assignee: Occlutech GmbH, Jena (DE)

( * ) Notice: Subject to any disclaimer, the term of this patent is extended or adjusted under 35 U.S.C. 154(b) by 494 days.

(21) Appl. No.: 17/595,385

(22) PCT Filed: May 22, 2020

(86) PCT No.: PCT/EP2020/064330
§ 371 (c)(1),
(2) Date: Nov. 15, 2021

(87) PCT Pub. No.: WO2020/234470
PCT Pub. Date: Nov. 26, 2020

(65) Prior Publication Data

US 2022/0202401 A1 Jun. 30, 2022

(30) Foreign Application Priority Data

May 22, 2019 (EP) .................................... 19175841

(51) Int. Cl.
*A61B 17/00* (2006.01)

(52) U.S. Cl.
CPC ............................... *A61B 17/0057* (2013.01); *A61B 2017/00526* (2013.01); *A61B 2017/00592* (2013.01); *A61B 2017/00606* (2013.01)

(58) Field of Classification Search
CPC ........... A61B 2017/00526; A61B 2017/00592; A61B 2017/00606
See application file for complete search history.

(56) References Cited

U.S. PATENT DOCUMENTS 5,944,738 A * 8/1999 Amplatz ............ A61B 17/0057 606/213
8,100,938 B2 1/2012 Figulla et al.
(Continued)

FOREIGN PATENT DOCUMENTS

EP 2 063 791 A0 3/2008
JP 2009000497 A 1/2009
(Continued)

OTHER PUBLICATIONS

WIPO, European Patent Office International Search Authority, International Search Report and Written Opinion mailed Sep. 30, 2020 in International Patent Application No. PCT/EP2020-064330, 28 pages.

(Continued)

*Primary Examiner* — Alexander J Orkin
(74) *Attorney, Agent, or Firm* — Enable IP, P.C.

(57) ABSTRACT

The invention discloses an occluder for a structural heart defect, comprising a tubular interlaced structure having a pitch that varies along an axial length of the occluder; a proximal element; a distal element; and an intermediate element extending between the proximal element and the distal element. According to one aspect, at least one transition section of the pitch, from a first pitch to a second pitch, is located closer to the intermediate element of the occluder than an outer circumference of at least one of the proximal elements and the distal element when the occluder is in a relaxed state. According to another aspect, the occluder is extendible from the relaxed state to an axially extended state wherein the load to extension ratio, measured in N/mm, provided by the occluder is less than about 0.75 when extended at least 2 mm.

20 Claims, 3 Drawing Sheets

(56) References Cited

U.S. PATENT DOCUMENTS

| | | | | |
|---|---|---|---|---|
| 8,313,505 | B2 | 11/2012 | Amplatz et al. | |
| 8,715,317 | B1 * | 5/2014 | Janardhan | A61B 17/12109 606/200 |
| 8,777,974 | B2 | 7/2014 | Amplatz et al. | |
| 2006/0224183 | A1 * | 10/2006 | Freudenthal | A61B 17/12031 606/213 |
| 2007/0043391 | A1 * | 2/2007 | Moszner | D04C 3/40 606/213 |
| 2007/0073337 | A1 * | 3/2007 | Abbott | A61B 17/0057 606/213 |
| 2007/0167980 | A1 * | 7/2007 | Figulla | A61B 17/12177 606/213 |
| 2007/0225760 | A1 * | 9/2007 | Moszner | D04C 1/06 606/213 |
| 2007/0265656 | A1 | 11/2007 | Amplatz et al. | |
| 2008/0033475 | A1 | 2/2008 | Meng | |
| 2008/0033478 | A1 * | 2/2008 | Meng | A61B 17/12168 604/104 |
| 2008/0200945 | A1 * | 8/2008 | Amplatz | A61B 17/0057 606/213 |
| 2008/0262518 | A1 * | 10/2008 | Freudenthal | A61L 31/08 606/151 |
| 2009/0018562 | A1 * | 1/2009 | Amplatz | A61B 17/12022 606/151 |
| 2009/0281610 | A1 * | 11/2009 | Parker | A61F 2/966 623/1.11 |
| 2010/0023048 | A1 * | 1/2010 | Mach | A61B 17/12177 606/200 |
| 2011/0295298 | A1 * | 12/2011 | Moszner | A61B 17/0057 606/191 |
| 2012/0046690 | A1 * | 2/2012 | Blom | A61F 2/203 606/213 |
| 2012/0271337 | A1 | 10/2012 | Figulla et al. | |
| 2012/0271348 | A1 * | 10/2012 | Tekulve | A61B 17/0057 606/213 |
| 2014/0257360 | A1 * | 9/2014 | Keillor | A61B 17/12172 606/198 |
| 2014/0309684 | A1 * | 10/2014 | Al-Qbandi | A61B 17/0057 606/213 |
| 2015/0066077 | A1 * | 3/2015 | Akpinar | A61B 17/0057 606/213 |
| 2015/0238333 | A1 | 8/2015 | Berez et al. | |
| 2017/0095254 | A1 | 4/2017 | Hewitt et al. | |
| 2019/0282359 | A1 * | 9/2019 | Dasnurkar | A61F 2/2418 |

FOREIGN PATENT DOCUMENTS

| | | | |
|---|---|---|---|
| JP | 2017511202 | A | 4/2017 |
| JP | 2019506230 | A | 3/2019 |
| WO | WO1997/042878 | A1 | 11/1997 |
| WO | WO2003/065934 | A2 | 8/2003 |
| WO | 2008036156 | A1 | 3/2008 |
| WO | 2009016265 | | 2/2009 |
| WO | WO2011/161136 | A1 | 12/2011 |
| WO | 2013041721 | A1 | 3/2013 |
| WO | WO2014/110589 | A1 | 7/2014 |
| WO | WO2014/150288 | A2 | 9/2014 |
| WO | 2015160721 | A1 | 10/2015 |
| WO | 2016038115 | A1 | 3/2016 |
| WO | WO2017-139702 | A1 | 8/2017 |
| WO | WO2017/214431 | A2 | 12/2017 |
| WO | WO2018/058033 | A1 | 3/2018 |
| WO | WO2018-112203 | A1 | 6/2018 |
| WO | 2019197569 | A1 | 10/2019 |

OTHER PUBLICATIONS

European Search Report for EP19175841.6, dated Feb. 4, 2020.

European Search Report for EP22161650.1, dated Jul. 6, 2022.

Examination Report for EP20726481.3, dated Aug. 7, 2024.

Extract from EPO Register of EP 20726481.3, https://register.epo.org/application?number=EP20726481, printed Feb. 24, 2025.

Extract from EPO Register of EP 22161650.1, https://register.epo.org/application?number=EP22161650&lng=en&tab=main, printed Feb. 21, 2025.

Japanese Office Action in JP2021-569850 dated Jan. 23, 2024.

Korean Office Action in KR 10-2021-7041101, dated Jan. 10, 2025.

Office Action mailed by the Japanese Patent Office on May 18, 2026 in corresponding Japanese Patent Application No. 2025-070837.

* cited by examiner

OCCLUDER WITH STRETCHABLE WAIST

RELATED APPLICATIONS

This application is the U.S. National Phase of and claims priority to International Patent Application No. PCT/EP2020/064330, International Filing Date May 22, 2020, entitled Occluder With Stretchable Waist, which claims priority to European Patent Application No. 19175841.6 filed May 22, 2019 entitled Occluder With Stretchable Waist; both of which are incorporated herein by reference in their entireties.

FIELD OF THE INVENTION

The present invention pertains to the field of intravascular and/or cardiac occluders and devices, such as Atrial septal defect (ASD) occluders, Patent Foramen Ovale (PFO) occluders, PDA (Patent Ductus Arteriosus) occluders, PLD (Paravalvular Leak Devices), TAVI (transcatheter aortic valve implantation) PLDs, VSD (Ventricular Septal Defect) occluders, LAA (Left Atrial Appendage) occluders, interatrial shunt devices, such as the AFR (Atrial Flow Regulator), fistula devices, and/or VP (vascular plug) devices. In particular, these devices are made of interlaced structures, preferably of braided wire structures.

BACKGROUND

Occluders provide generally for full occlusion and allow for minimally invasive procedures for treatment of a variety of structural heart or vascular diseases. Interatrial shunt devices, such as the AFR allow for a controlled flow across the device when implanted, see e.g. WO2016/038115A1. Fistula devices may provide a passage between two body lumens. Vascular plugs my provide for the occlusion of vessels. Interventional techniques for treatment of structural heart or vascular disease using intravascular and/or cardiac occluders and devices have become established routine.

Occluders for treatment of structural heart diseases may have a disc at one end of the device, or two discs, one at each end of opposing ends of a waist. The disc(s) may have enlarged diameters relative a waist. Normally, the disc(s) is/are used as the occluding part of the occluder.

An occluder having two discs can extend between two sides of a heart structure, such as a septum wall, a heart valve, an annulus of a heart valve, or between two vessels like the pulmonary artery and the aorta. The discs can be positioned on each side of the heart structure, preferably as retention units to keep the occluder in place when implanted. A waist can extend through the heart structure. Such heart structures can have great variability. To accommodate the large variability of, e.g., length and shape of anatomies, occluders with a single disc have commonly been used for treating some diseases. For single disc occluders, either the disc or the waist can be used as the occluding part. However, the anatomy may distort the occluding waist such that the occluding efficacy of the device is distorted. It may be challenging to firmly seat the occluder in the anatomy.

In case an occluder with two discs, designed for a certain clinical/anatomical length, is used in a situation actually requiring an extendable length of the waist to suit the anatomy, the discs may be distorted due to the stiffness of the waist. This could deteriorate the occluding efficacy provided by the discs. Other structural heart diseases are treated with occluders that have a uniform diameter, or only a 5 single disc.

In WO 2017/139702A1, a vascular occlusion device is disclosed having petals of varying pitch. In U.S. Pat. No. 8,313,505 B2, a vascular occluder is disclosed of a single pitch. In WO 2014/150288 A2, a vascular treatment device is disclosed controlling a braid angle to control porosity of a device. In WO 2018/058033A1 an LAA occluder is disclosed having a multilayer braid with different pitches. In WO 2011/161136A1 a medical implant is disclosed being assembled of different braided segments. In WO 97/42878 A1, occlusion devices are disclosed made of a tubular braid having a single pitch. In EP 2 063 791 A1 and corresponding WO 2008/036156 A1, a cerebral vasculature device is disclosed where a braid angle of a tubular braid not at end sections of the device is controlled to limit expansion of certain sections of the device. In WO 2014/110589 A1 an occlusion device with variable pitch is disclosed while the disclosure is silent about the purpose and function of the variable pitch in the device. In WO 2017/214431 A2, a braided vaso-occlusive member is disclosed, and a variable pitch of a braid is disclosed, while the disclosure is silent about the purpose and function of the variable pitch in the device. In WO 03/065934 A2 a braided modular stent is disclosed where different braiding angles provide different radial strength of the stent. In WO 2018/112203 A1 a stent with a polymeric electrospun coating is disclosed. In US 2015/238333 A1, a vascular aneurysm stent device is disclosed.

Certain anatomies are not suitable for occlusion with any of the previously described occluders.

Also, the length of the anatomical structure to be occluded by the waist may change during the duration of life of an implanted occluder. For instance, structures can dilate in structural heart diseases. Also, contractions can occur, e.g. during cardiac sinus rhythm or during fibrillation. For instance, atrial appendices may contract or expand. Cardiac walls can thicken. Generally, known occluders cannot cope with such changing anatomical situations resulting tension on the surrounding implantation tissue, potentially leading to ruptures of tissue, undesired leakage at implantation sites, or even embolization of devices with dire consequences for the patient.

Therefore, there is a need for an occluder with increased flexibility for treatment of anatomies having a larger variability, such as length and/or shape.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing occluder according to the appended patent claims.

The present invention is defined by the appended claims only, in particular by the scope of appended independent claim(s). Reference(s) to "embodiments" throughout the description which are not under the scope of the appended claims merely represents possible exemplary executions and are therefore not part of the present invention. In one aspect, the present disclosure comprises an occluder with a tubular interlaced structure having a pitch that varies along an axial length of the occluder, and where at least one transition section of the pitch is located closer to a center axis or an intermediate member of said occluder than an outer circumference a proximal element and/or a distal element when the occluder is in a relaxed state. The Occluder comprises a continuous tubular braided structure made of an integral base body of at least one wire and having a pitch, said pitch varies along an axial length of the base body with at least one pitch transition section. The occluder being heat set to have a shape preferably including a proximal retention element having an outer circumference and a distal inner diameter at a first transition section in a relaxed state of the occluder. The shape preferably includes a distal retention element having an outer circumference and a proximal inner diameter at a second transition section in the relaxed state of the occluder. The shape preferably includes an intermediate element extending between the first and second transition sections of the proximal retention element and the distal retention element. The at least one pitch transition section of said pitch from a first pitch to a second pitch is preferably located closer to the intermediate element or central axis of said occluder than to the outer circumference of at least one of the proximal elements and the distal element when the occluder is in the relaxed state. Preferably a position of at least one of said transition sections is closer to said central axis, and a diameter of said intermediate element is reduced from a relaxed diameter thereof, when the occluder is in an axially extended state.

In another aspect, the present disclosure comprises an occluder that is extendible from the relaxed state to an axially extended state, which is longer in the longitudinal direction of the occluder than the relaxed state, and wherein the load to extension ratio, measured in N/mm, provided by the occluder is less than about 0.75 when extended at least 2 mm. The first aspect and the second aspect can form mutually exclusive embodiments or be combined into a single embodiment.

In another aspect of the present disclosure, a method of manufacture an occluder is provide. The method includes forming an integral base body of at least one wire providing a continuous tubular braided interlaced structure having a pitch, the pitch varies along an axial length of the occluder base body with at least one pitch transition section. The method includes heat setting the base body to have a shape preferably including a proximal retention element having an outer circumference and a distal inner diameter at a first transition section in a relaxed state of the occluder. The shape preferably includes a distal retention element having an outer circumference and a proximal inner diameter at a second transition section in the relaxed state of the occluder. The shape preferably includes an intermediate element extending between the first and second transition sections of the proximal retention element and the distal retention element. The at least one pitch transition section of the pitch from a first pitch to a second pitch is preferably located closer to the intermediate element or central axis of the occluder than to the outer circumference of at least one of the proximal elements and the distal element when the occluder is in the relaxed state. Alternatively or in addition, the occluder is extendible from the relaxed state to an axially extended state, which is longer in the longitudinal direction of the occluder, than the relaxed state, and wherein the load to extension ratio, measured in N/mm, provided by the occluder is less than about 0.75 when extended at least 2 mm, without distortion of the proximal or distal retention elements.

Embodiments of the invention provide an occluder comprising at least one wire; a tubular interlaced structure made of at least one wire and having a pitch, wherein the pitch varies along an axial length of the occluder; a proximal element having an outer circumference and an inner diameter in a relaxed state of the occluder; a distal element having an outer circumference and an inner diameter in the relaxed state of the occluder; and an intermediate element extending between the proximal element and the distal element.

According to a first aspect, at least one transition section of the pitch, from a first pitch to a second pitch, is located closer to the intermediate element or the central longitudinal axis of the occluder than the outer circumference of at least one of the proximal element and the distal element when the occluder is in the relaxed state.

According to a second aspect, the occluder is extendible in its longitudinal direction, from the relaxed state to an axially extended or elongated state, which is longer in the longitudinal direction of the occluder than the relaxed state. A load to extension ratio, measured in N/mm, provided by the occluder is less than about 0.75 when extended at least 2 mm.

In various embodiments, the first aspect and the second aspect may be mutually exclusive embodiments or combined into a single embodiment. Each of the first aspect and second aspect, separately or together, may be combined with the following embodiments.

In an embodiment, at least one transition section of the pitch may be located between the outer circumference and the inner diameter of at least one of the proximal element and the distal element when the occluder is in the relaxed state.

In an embodiment, at least one of the proximal element and the distal element comprises at least the first pitch, and the intermediate element comprises the second pitch only along an axial length of the intermediate element.

In an embodiment, at least one of the outer circumferences of the proximal element and the distal element is substantially constant when the inner diameter is reduced upon stretching the occluder in the longitudinal direction.

In an embodiment, at least one of the proximal element and the distal element comprises the first pitch only.

In an embodiment, the intermediate element comprises the first pitch and the second pitch along an axial length of the intermediate element.

In an embodiment, the occluder is extendible from the relaxed state to an axially extended state, which is longer in the longitudinal direction of the occluder than the relaxed state.

In embodiments, the load to extension ratio, measured in N/mm, provided by the occluder is less than 0.5 N/mm, preferably less than 0.75 N/mm, even more preferably less than 0.25 N/mm, when extended from at least 2 mm and up to about 6 mm.

In embodiments, a reduction of a cross-sectional diameter of the intermediate element is less than 60%, preferably less than 40%, when the occluder is extended from the relaxed state to the extended state.

In embodiments, the outer circumference of at least one of the proximal element and the distal element is substantially constant when the occluder is extended in length more than 50% of the relaxed state and up to about 150% of the relaxed state.

In embodiments, the intermediate element is at least partly straight or waisted in shape, such as cylindrical or conical, bell-shaped, or hourglass shaped, relative a longitudinal axis of the occluder when the occluder is in the relaxed state.

In embodiments, the occluder is for instance one of PDA occluders, PLDs, TAVI-PLDs, VSD occluders, Atrial septal defect (ASD) occluders, Patent Foramen Ovale (PFO) occluders, LAA occluders, interatrial shunt devices, such as the AFR (Atrial Flow Regulator), fistula devices, or vascular plug (VP) devices.

Embodiments of the invention provide an occluder that can be used for occluding anatomies having a wide variety of shapes, and for which occlusion by surgery hitherto may have been the only option available. Particularly, the stretchability of the present invention provides for an occluder that may adapt to the shape of a large variety of anatomies and is therefore very flexible. For example, when used with proximal and/or distal elements of enlarged diameter relative a waist in between, the occluder may provide occlusion with the proximal and distal elements provided at respective ends of an intermediate element. Occlusion may be enhanced by suitable coatings and/or fabric patches known for the skilled person.

The term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of, will be apparent and elucidated from the following description of embodiments of the present invention, reference being made to the accompanying drawings, in which.

DESCRIPTION OF EMBODIMENTS

Figure 1A:
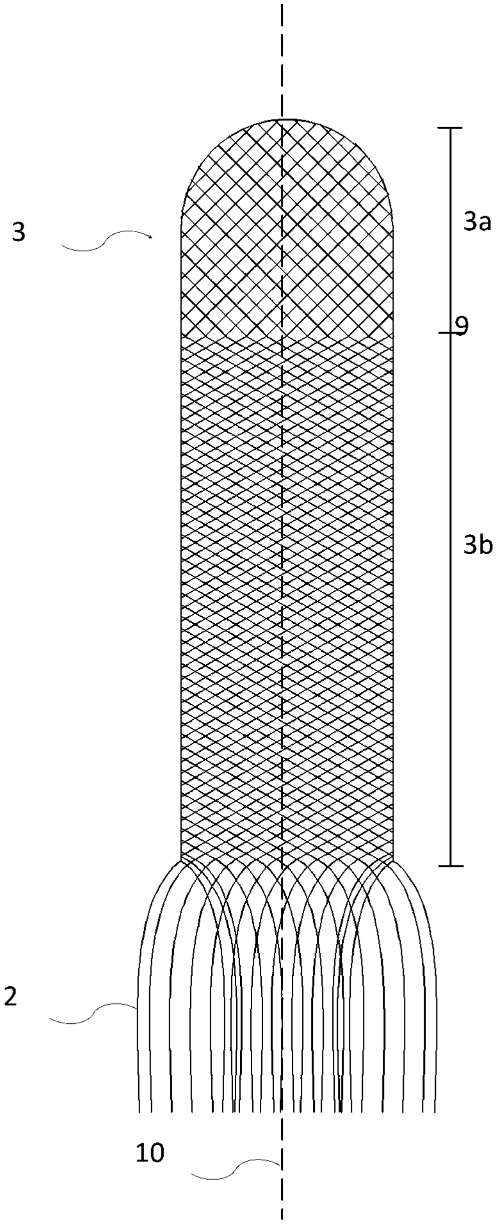
FIG. 1*a* is a side view of an embodiment of a base body having an example of basic shape of a tubular interlaced structure before heat setting to for the relaxed occlude 1.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention as defined by the appended claims to those skilled in the art. The terminology used in the detailed description of the embodiments illustrated in the accompanying drawings is not intended to be limiting of the invention. In the drawings, like numbers refer to like elements.

The present description of the current invention is given with reference to an occluder 1, which is exemplified in the embodiment of a PDA occluder. Other occluders of the disclosure have similar shape and function, e.g. a VSD such as a mVSD (muscular Ventricular Septal) occluder having the improvement of the present disclosure, where a conventional mVSD is discussed below for comparative measurements to occluders not having the present improvement(s). It should therefore be born in mind, however, that the present invention is not limited strictly to the illustrated embodiments, but includes additional embodiments that form other types of occluders, such as PDA occluders, PLDs, TAVI-PLDs, VSD occluders, Atrial septal defect (ASD) occluders, Patent Foramen Ovale (PFO) occluders, LAA occluders, interatrial shunt devices, such as the AFR (Atrial Flow Regulator) allowing a controlled left/right heart blood flow across an atrial wall, fistula devices, or vascular plug (VP) devices, a fistula channel (at least partial flow occluding or flow directing across the fistula) occluder.

The invention will be described with regard to a first aspect and a second aspect and embodiments thereof. The first aspect and the second aspect may form mutually exclusive embodiments. However, in some embodiments, the first aspect and the second aspect are combined into a single embodiment, which may be further defined by the detailed embodiments described herein. Structures that are common to the first aspect and the second aspect will first be described.

Figure 1B:
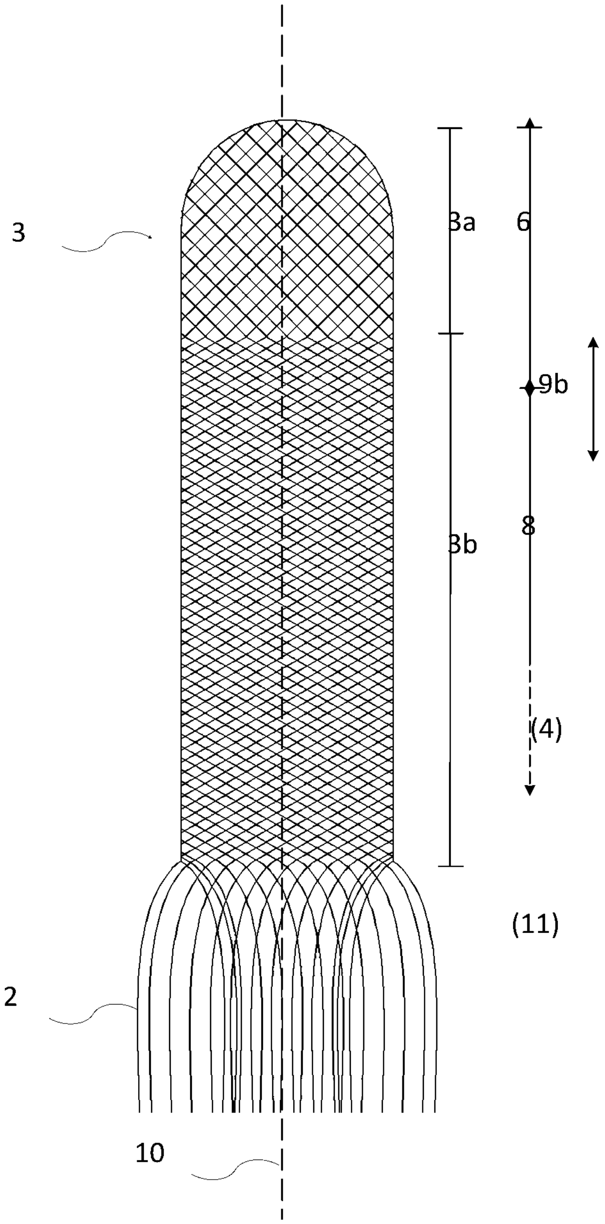
FIG. 1*b* is a side view of the base body of FIG. 1*a* with comparative indications of an example which portions of the base body will be located in the occluder 1 when given the desired shape by a suitable heat setting process.

As illustrated in FIGS. 1*a* and 1 *b*, a base body for an occluder 1, comprises at least one wire 2 that may be formed into a tubular interlaced structure 3 (FIG. 1*a*) made of the at least one wire 2. The base body is made of a single, integral and continuous interlaced structure 3, e.g. a single braid with two opposed ends. The interlaced structure 3 may also be made of a single wire. The wire 2 may also be referred to as a strand. The wire may be made of metal. The wire may be made of a suitable polymer material. The strand may be made as a single core massive filament or may be built of sub-elements forming the strand (multi filaments), like a braided multi-filament strand similar to cable strand technology. The wire 2 may be formed by a shape memory material, such as a shape memory metal, for example Nitinol. Particularly, the wire 2 may be formed by a shape memory material with superelastic properties.

The tubular interlaced structure 3 is generally interlaced by a weaving technology. Preferably the tubular interlaced structure 3 is woven to provide the tubular interlaced structure 3 as a tubular braid. The tubular braid may be provided by known braiding technologies; however, the sections of varying pitch and/or elasticity are provided by the presently disclosed improvement. A suitable example of a braiding technique for a sack shaped base body with a single pitch is disclosed in US2007/0225760A1, of the same applicant as the present application, which is incorporated by reference herein in its entirety for all purposes. The skilled person will know how to modify the teaching in US2007/0225760A1 to produce a base body in accordance with the improvement disclosed in the present disclosure.

The wire(s) of the tubular interlaced structure 3 are structured to have pitch, which is the longitudinal distance required for one revolution of the wire around the tubular interlaced structure 3. As can be seen in FIGS. 1*a* and 1 *b*, the pitch may vary along an axial length of the occluder 1. At a first section 3*a*, the pitch may be larger than the pitch at a second section 3*b*. This provides for varying the extensibility (stretchability) or elasticity of the tubular interlaced structure 3 along its length. The first, second (and further e.g. third) sections of the tubular interlaced structure 3 may thus be given a different extensibility (stretchability) by the varying pitch. For instance, the first section can be given a pitch to be less extensible (stretchable) than the second portion 3*b*. A third section (if present) can be given a different pitch than the first portion 3*a* or the second portion 3*b*. The third section may be given the same pitch as the first section 3*a* in an example. Further section may be defined accordingly by varying the pitch in the sections relative the other sections in the base body of the tubular interlaced structure 3.

For example, the pitch of the wires (i.e., the angle defined between the turns of the wires and the axis of the interlaced structure) and the pick of the tubular interlaced structure 3 (i.e., the number of wire crossovers per unit length) may be adjusted as desired for a particular application. For example, the pitch of the wires can be about 90°-130° such as about 100°. Also, as an example, the pick count in the second section 3*b* can be about 7-12 picks/5 mm, such as about 9 picks/5 mm, when the occluder 1 is in the relaxed shape. When the occluder has been stretched about, 4-6 mm, the pitch of the wire can be about 50°-90° and/or the pick count in the second section 3*b* can be about 12-16 picks/5 mm, such as about 14 picks/5 mm. At the same time, the pitch and/or the pick of the first section 3*a* of the heat shaped occluder 1 can be constant in both the relaxed and stretched shape. Alternatively, or additionally, the wires in the first section 3*a* may be interlaced to form petal like shapes. Hence, the pick of the first section 3*a* may be substantially constant when the occluder is in the relaxed shape as well as in the stretched state, whereas the second section has a variable pick in the relaxed shape relative the stretched state.

FIG. 1*a* illustrates the tubular interlaced structure 3 made of a braid of multiple wires in its basic shape before heat treatment and shaping the occluder 1 to its relaxed shape. Moreover, the base body interlaced structure 3 of FIGS. 1*a* and 1 *b* illustrates an embodiment which comprises a first section 3*a*, and a second section 3*b*, wherein the first section 3*a* is distal of the second section 3*b*. A pitch transition section 9 is present between sections when sections have different (varying) pitch.

In other embodiments, the base body interlaced structure 3 comprises a third section (not shown in FIG. 1*a* or 1*b*), which is formed proximal of the second section 3*b*. The third section may have a pitch that is different from the pitch of the second section 3*b*, such as larger than the pitch of the second section 3*b*. In other embodiments, the pitch of the third section is smaller than the second section 3*b*.

Other embodiments may have further sections, accordingly.

The heat set occluder 1 will then have the same sections defined by the base body along its longitudinal axis after heat setting the relaxed shape of the occluder 1. The sections of the base body interlaced structure 3 may not correspond 1:1 to sections of the heat set occluder. For instance, the pitch transition section 9 is fixed along the base body and thus also along the heat set occluder 1. However, the transition from an occluder element like an end disc 6, to an adjacent occluder element, like the intermediate section 8 (also called "waist" of an occluder) at a transition section 9*b* as detailed described below), may be present at different transition sections or positions 9*a*, 9*b* along the longitudinal axis of the heat set occluder than the pitch transition section 9. The position of a transition section 9*a*, 9*b* along the longitudinal axis and/or axial position of the occluder 1, may even be variable. For instance, the variability of the position of the transition section 9*a*, 9*b* may be determined by the stretching status of the occluder 1, see below.

Hence, an element of the occluder 1, like the discs 4, 6, may have two or more sections of different pitch sections (like 3*a*, 3*b*) along their extension. For instance, the inner disc portion of a double folded disc, like distal disc 6, may include a pitch transition 9 between sections of the base body, while the transition section 9*b* to the waist 8 is positioned more innerwards towards the central axis 10 of the occluder 1, as can be seen in FIGS. 2 to 5.

Figure 2A:
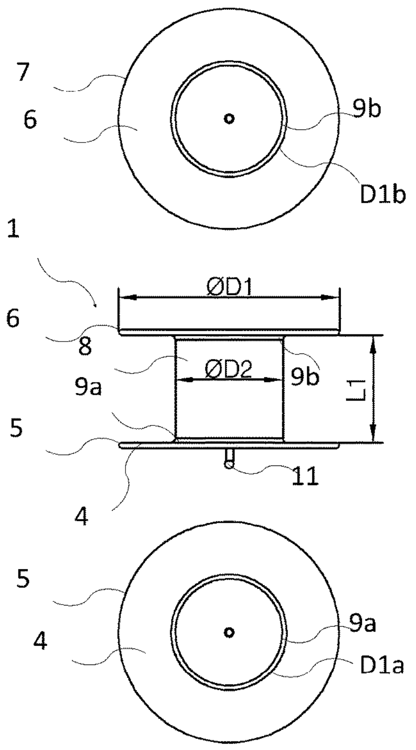
FIG. 2*a* is a side view and cross-sectional views taken at the centre of an embodiment of the occluder, across the longitudinal direction and viewed towards the proximal and distal ends, respectively, when the occluder is in the relaxed state.

Moreover, the position of the transition section 9*a*, 9*b* is variable, see e.g. a comparison of FIGS. 2*a,b* and 3*a,b* as well as 4*a,b* and 5*a,b*, respectively.

Hence, the length of the waist 8 may be variable partly thanks to the variable position of the transition section 9*a*, 9*b*, and partly to the different pitch of the first section 3*a* and second section 3*b*.

In addition, the extensibility (stretchability) or elasticity of the waist 8 may be chosen to further promote that the waist stretches before a deformation of the end portion/outer diameter of a disc occurs, see below.

Figure 3A:
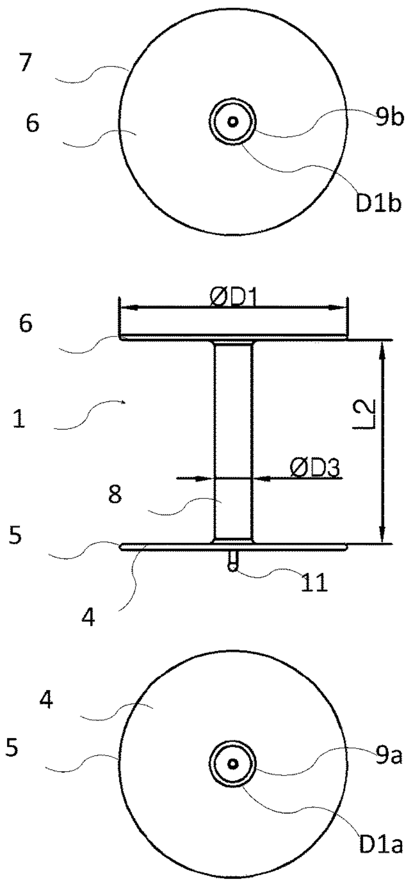
FIG. 3*a* is a side view and cross-sectional views taken at the centre of the occluder of FIG. 2*a*, across the longitudinal direction and viewed towards the proximal and distal ends, respectively, when the occluder is in an axially extended or elongated state.
Figure 3B:
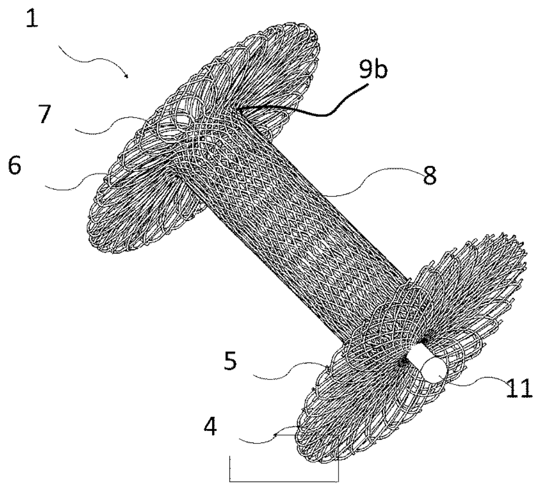
FIG. 3*b* is a perspective view of the occluder of FIG. 2*a* in the axially extended or elongated state.
Figure 4A:
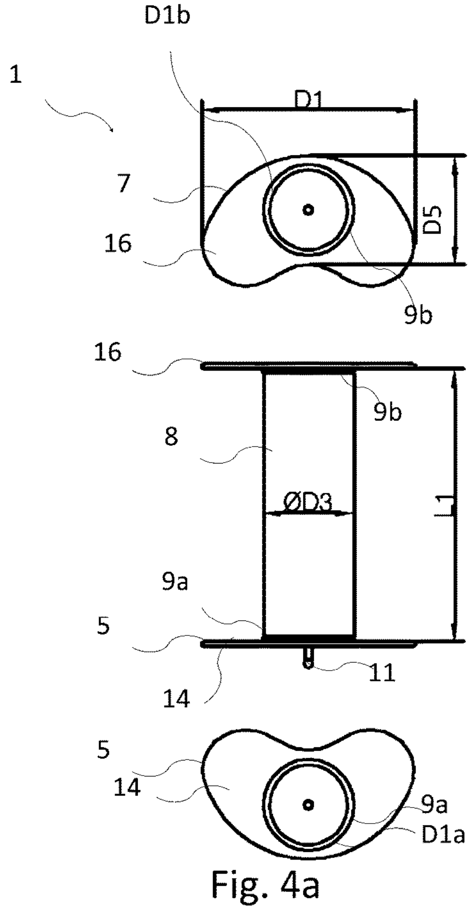
FIG. 4*a* is a side view and cross-sectional views taken at the centre of an embodiment of the occluder, across the longitudinal direction and viewed towards the proximal and distal ends, respectively, when the occluder is in the relaxed state.
Figure 5A:
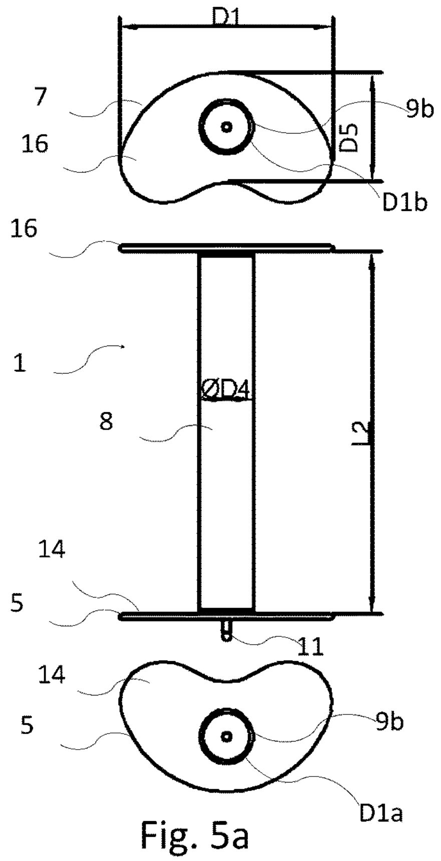
FIG. 5*a* is a side view and cross-sectional views taken at the centre of the occluder of FIG. 4*a*, across the longitudinal direction and viewed towards the proximal and distal ends, respectively, when the occluder is in an axially extended or elongated state.
Figure 4B:
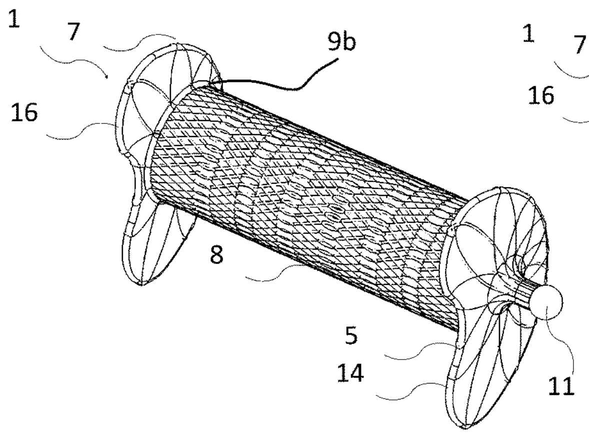
FIG. 4*b* is a perspective view of the occluder of FIG. 4*a* in a relaxed state.
Figure 5B:
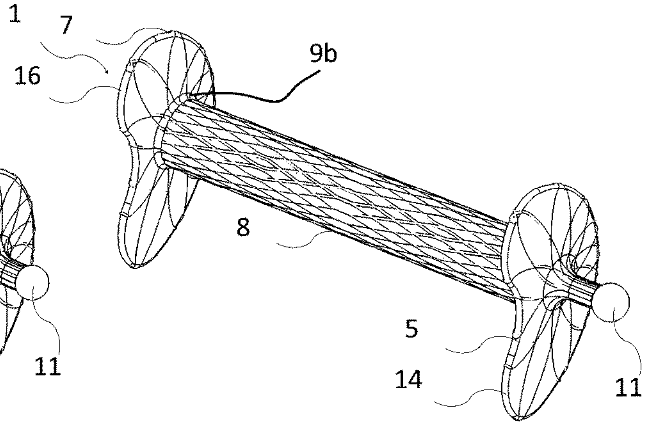
FIG. 5*b* is a perspective view of the occluder of FIG. 4*a* in the axially extended or elongated state shown in FIG. 5*a*.

In some embodiments, the pitch of the first section 3*a* and the third section is the same, which provides for applying substantially equal forces to the second section 3*b* when the occluder 1 is stretched or elongated as will be described below. In other embodiments, the first section 3*a*, and optionally the third section, may be formed by wires that are petal shaped, such as is illustrated in FIGS. 4*b*, 5*b*. Such a shape may also be utilized for the embodiment illustrated in FIGS. 2*b*, 3*b*.

The interlaced structure 3 of FIG. 1*a* forms a basic shape that may be heat treated in one or multiple steps to form the shape of the occluder in the relaxed state or non-elongated state and obtain the characteristics of the occluder as will be further described below. Heat treatment of shape memory materials, such as Nitinol, is known as such and will not be further described herein. The relative position of portions of an example of an occluder can be seen in FIG. 1*b*.

In addition to the varying pitch sections, the extensibility (stretchability) or elasticity of the tubular interlaced structure 3 may be further defined by the heat setting process, which can be done in sections with different parameters, as the skilled person will know how to implement. The extensibility (stretchability) or elasticity may thus be defined variable along the longitudinal axis of the heat set occluder 1. For instance, the intermediate element 8 may have a higher extensibility (stretchability) than one or two end portions, like discs 4, 6.

After heat treatment, the occluder is generally self-expandable. When collapsed, e.g. during delivery in a catheter sheath, it will resiliently return to the heat set relaxed shape, if not constrained further. The occluder may be re-collapsed, entirely or at least partly, whereupon it may self-expand again. Preferably a superelastic material is provided for the wire strand(s), like Nitinol.

Figure 2B:
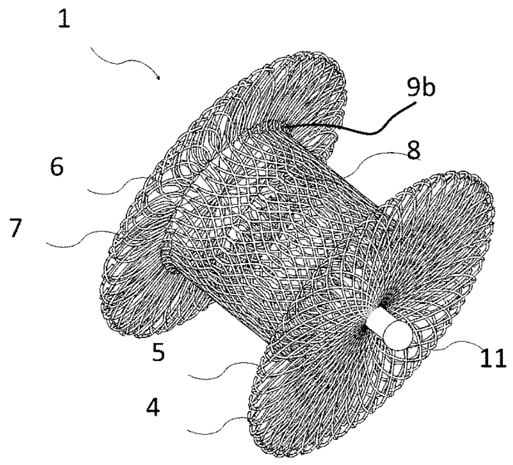
FIG. 2*b* is a perspective view of the occluder of FIG. 2*a* in a relaxed state.

FIGS. 2*a*-2*b* illustrate a relaxed or non-elongated state of the occluder. The occluder 1 may comprise a proximal element 4 having an outer circumference 5 and an inner diameter D1*a* in the relaxed state of the occluder 1. Additionally, or alternatively, the occluder 1 may comprise a distal element 6 having an outer circumference 7 and an inner diameter D1*b* in the relaxed state of the occluder 1. An intermediate element 8 may extend between the proximal element 4 and the distal element 6.

In particular, the distal element 6 may be a distal retention element. In particular, the proximal element 4 may be a proximal retention element. Retention means the ability to keep the occluder 1 in place when implanted. For instance, the retention element may be a retention disc.

Each of the proximal element 4 and the distal element 6 may form a disc of the occluder 1.

The occluder 1 may comprise the proximal element 4 and/or the distal element 5, i.e. comprise a proximal disc and/or a distal disc.

The proximal/distal element 4, 6 may e.g. be substantially circular, oval, substantially square, kidney shaped (e.g. for a TAVI PLD) etc.

Furthermore, the proximal/distal element may be cupped, i.e. the outer circumference thereof may be curved in the proximal and distal direction of the occluder 1.

Furthermore, the proximal/distal element may be dome shaped (convex outer surface at end surface).

In some embodiments, the proximal/distal element 4, 6 is curved from its center. In other embodiments, only a portion of the proximal/distal element 4, 6 is curved.

Furthermore, the proximal/distal element may be provided additionally or alternatively with a recessed portion, e.g. to "hide" connections elements, like welded or clamped ends of wires and prevent from protruding beyond the end surface, thus providing improved endothelialization and/or reduced risk of thrombus to attach to the occluder surface when implanted.

The intermediate member 8 may form a waist of the occluder 1. The maximum outer diameter of the intermediate member 8 may be smaller than the maximum outer diameter of the proximal element 4 and the distal element 6.

In some embodiment, the intermediate element 8 comprises the first pitch and the second pitch along an axial length of the intermediate element 8. Furthermore, the intermediate section 8 may have a varying pitch along its length, such one or several sections with larger and smaller pitch along its length, as can be seen in FIGS. 2*b* and 3*b*, respectively. This further enhances elastic property of the intermediate section 8. The intermediate section 8 has in the example a substantially higher elasticity in the longitudinal direction of the occluder than the proximal element 4 and the distal element 6.

According to the first aspect, at least one pitch transition section 9 of the pitch from a first pitch to a second pitch is located closer to the inner diameter D1*a* and/or the center axis 10 of the occluder than the outer circumference 5, 7 of at least one of the proximal element 4 and the distal element 6 when the occluder 1 is in the relaxed state or non-elongated state. The pitch transition 9 occurs in the example on the inner disc portion (oriented away from an end of the occluder and towards a longitudinal middle/center of the occluder) of a double folded distal element in form of a disc element. The distal element may have an outer diameter or axial circumference. The pitch transition 9 is located closer to the inner diameter D1*a* and/or the center axis 10 of the occluder than the outer circumference 5, 7. This contributes to the higher extensibility (stretchability) or elasticity of the intermediate member 8 than at least one of the proximal element 4 and the distal element 6.

According to the second aspect, the occluder 1 may be extended or elongated from the relaxed state to the axially extended state, which is longer in the longitudinal direction of the occluder, than the relaxed state. The occluder 1 may have a load to extension ratio, measured in N/mm. The load to extension ration may be measured as is described below. The load to extension ratio provided by the occluder 1 may be less than about 0.75 N/mm when the occluder is extended or elongated at least 2 mm in the axial direction along the central or longitudinal direction 10 of the occluder 1. This load to extension ratio over this length expansion/occluder stretching range may be provided without substantially distorting the proximal element 4 and/or the distal element 4. The proximal element 4 and/or the distal element 4 are generally not distorted when the disc shape is maintained and/or at least the outer diameter/circumference thereof is not changed from the relaxed heat set shape. Thus, the retaining capability provided by distal element(s) to stay in implantation place, when occluder 1 is implanted over a large range. Hence, the ratio defines the higher extensibility (stretchability) or elasticity of the intermediate member 8 than that of at least one of the proximal element 4 and the distal element 6, respectively. The occluder 1 thus is advantageously adaptable to anatomical variations, even during the (long-term) duration of being implanted, while having maintained retainability (as the proximal and/or distal element 4,6 are not distorted. When being stretched further, beyond the end of the range of the axially extended state, the occluder may distort in shape (which is desired for instance when collapsing the occluder into a delivery sheath for implantation).

In the following, embodiments will be described that may be combined with the first aspect only, the second aspect only, or the first aspect and the second aspect in combination.

In some embodiments the load to extension ratio provided by the occluder 1 is less than 0.5 N/mm, preferably less than 0.75 N/mm. In some embodiments, it may even be less than 0.25 N/mm. The load to extension ration may be provided when the occluder 1 is extended or elongated a predefined length in its longitudinal direction. The predefined length may e.g. be within at least 2 mm and up to about 6 mm. The occluder 1 is highly stretchable over a large range, compared to prior devices, before the distortion mentioned above occurs.

FIG. 2*a* is a side view of the occluder 1 (center view), and cross-sectional views taken across the intermediate section 8 and viewed towards the proximal element 4 (bottom view) and towards the distal element 6 (top view). FIG. 3*a* includes similar views taken of the occluder 1 in the extended state. Each of the proximal element 4 and the distal element 6 may be formed by a double layer of the interlaced structure 3 with an outer edge of the double layer forming the outer diameter or circumference 5, 7 respectively. Hence, the transition section 9*a* of the proximal element 4 may be located on a distal side of the proximal element 4, as is illustrated at the bottom view of FIG. 2*a*. Similarly, the transition section 9*b* of the distal element 6 may be located on a proximal side of the distal element 6, as is illustrated at the top view of FIG. 2*a*.

As can be seen on the Figures, the transition section 9*a*, 9*b* may have a variable axial position (distance to longitudinal center axis 10) in dependence of an elongation state of the occluder 1 while the outer diameter or circumference 5,7 remains substantially constant upon the elongation within a large extension/stretching range of occluder 1.

Generally, the occluders of the disclosure avoid a transition segment with reduced diameter. The occluders in certain embodiments do not have a transition segment with reduced diameter, in particular they do not have a transition segment between an end element like the distal or proximal element 6,4 and the intermediate element 8. The varying pitch and/or sections of fabric softness provide for an enhanced flexibility of sections of the occluder to each other. In particular, not only the stretchability is better than in prior devices, but also a potential improved pivoting or tilting movement of elements of the occluder relative each other is provided by the arrangement of braid pitch transition segments and relative position of transition segments 9*a*, 9*b* between occluder elements. A transition segment with reduced diameter may thus be omitted, while it can be present in some embodiments.

In some embodiment, the at least one transition section 9 of the pitch is located between the outer circumference 5, 7 and the inner diameter D1*a*, D1*b* of at least one of the proximal element 4 and the distal element 6 when the occluder 1 is in the relaxed state.

For example, at least one of the proximal element 4 and the distal element 5 may comprise at least the first pitch. The intermediate element 8 may comprise the second pitch only along an axial length of the intermediate element 8. Hence, the intermediate element 8 may in an example be formed of only the second section 3*b* of the tubular interlaced structure 3. Similarly, the proximal element 4 and/or the distal element 5 may be formed of only the first section 3*a*/third section of the interlaced structure 3.

Hence, the transition section 9 may bridge the intermediate element 8 and the proximal/distal element 4, 6. Thus, in some embodiments, at least one of the proximal element 4 and the distal element 6 comprises the first pitch only.

FIGS. 3*a*-3*b* illustrate an extended or elongated state of the occluder 1, wherein the axial length of the occluder 1 is extended or elongated. In this state, the intermediate section 8 of the occluder is extended/elongated. The occluder is longitudinally stretched. However, the axial length or thickness in the longitudinal direction of the proximal element 4 and/or the distal element 6 remains substantially constant, not distorted. Furthermore, the inner diameter D3 of the intermediate element 8 in the elongated state of the occluder 1 is reduced relative the relaxed state, whereas the outer circumference of the proximal element 4 and/or the distal element 6 remains substantially constant, not distorted. D3<D2 when L2>L1 while D1 is substantially unchanged. This is due to the varying stiffness of the intermediate element 8 and the proximal element 4 and/or the distal element 6, resulting in the different stretchability respectively.

As is illustrated in FIGS. 2*a*-3*b*, at least one of the outer circumference 5, 7 of the proximal element 4 and the distal element 6, respectively, is substantially constant when the inner diameter D1*a*, D1*b* is reduced upon stretching or elongating the occluder 1 along its longitudinal or central axis 10. This may e.g. be provided by providing the varying pitch of the first section 3*a*, the second section 3*b*, and optionally of the third section of the tubular interlaced structure 3.

In some embodiments, a cross-sectional diameter of the intermediate element 8 when the occluder is extended in axial length, from the relaxed state to the extended state, is reduced by less than 60%, preferably less than 40%, from diameter D2 to diameter D3, without distortion described above.

Similarly, in some embodiments, the outer circumference or diameter 7 of at least one of the proximal element 4 and the distal element 6 is substantially constant when the occluder 1 is extended in length, from a non-extended or relaxed length L1, by more than 50% of the relaxed state and up to about 150% of the relaxed state to an extended or elongated length L2.

In the embodiments illustrated in FIGS. 2*a*-2*b*, the intermediate element 8 is at least partly straight or waisted in shape, such as cylindrical or conical. However, in other embodiments, the intermediate element 8 is bell-shaped or hourglass shaped relative the longitudinal axis or center axis 10 of the occluder 1 when the occluder 1 is in the relaxed state. The shape of the intermediate section 8, as well as the shape of the proximal element 4 and/or the distal element 6, may be shaped by one or several molds during heat treatment in one or multiple steps and using the same or different temperatures during the heat treatment of the shape memory material. The skilled person will select suitable setting temperatures and setting times as well as distribution of setting heat to obtain a desired device as disclosed herein, depending on the actual material chosen for the occluder 1, the chosen pitches and their distribution along the base body, distribution of occluder elements along the longitudinal axis of the occluder, desired softness or hardness of the fabric at desired sections of the occluder 1, etc. This is to contribute to the larger elasticity of the intermediate element 8 mentioned above, compared to at least the outer side oriented towards the end of occluder 1 of the proximal element 4 and the distal element 6, respectively. The intermediate element may thus be heat set to have a softer fabric than the element(s) 4,6. The intermediate element 8 may have sections with both the first pitch and the second pitch. Such an intermediate element may have a softer fabric by heat treatment than an adjacent element. The intermediate element 8 may thus have two sections of pitches with the same braided fabric softness/elasticity/stretchability being different from the braided fabric softness/elasticity/stretchability of the adjacent element 4, 6. The distal and/or proximal element 6, 4 may have sections with both a first and second pitch. The first pitch may be identical to a third pitch. After heat treatment, the occluder 1 is removed from molding element (s) and substantially retains its relaxed shape after being deformed.

At least one of the ends of the occluder 1 may comprise an attachment element 11 for attaching the occluder 1 to a delivery device for catheter-based delivery. The attachment element 11 may be a weld, such as a laser weld. In the illustrated embodiments, the base body interlaced structure 3 is sack shaped, i.e. the wire(s) 2 start at the proximal end, is interlaced to the distal end, and then returns by interlacing to the proximal end. In other embodiments, the interlaced structure 3 is tubular with an attachment element, such as a clamp, that bundles free ends of the wires 2 at each end. The attachment element 11 for attaching the occluder 1 may be provided at the central axis 10 of the occluder 1. The attachment element 11 for attaching the occluder 1 may also be provided off-center from the central axis 10, such as at an AFR. In WO09016265A2, of the same applicant as the present application, which is incorporated by reference herein in its entirety for all purposes, a manufacturing method for bundling free ends of wires 2 and fixation the ends together is disclosed. Hence, in such embodiments, one end of the wire 2 is located at the distal end of the occluder and the other end of the wire 2 is located at the proximal end of the occluder 1 (not shown).

FIGS. 4*a*-4*b*, 5*a*-5*b* illustrates an embodiment wherein with an alternative shape of the outer circumference of the proximal element 14 and the distal element 16. The intermediate element 8 has the same shape as described with regard to FIGS. 2*a*-3*b*. Furthermore, the proximal element 14 and the distal element 16 and the transition section 9*a*, 9*b* to the intermediate element 8 may be designed as has been described with regard to FIGS. 2*a*-3*b*. The proximal element 14 and the distal element 17 have a first diameter D1 and a second diameter D5 as illustrated. Hence, elements having the same configuration as the configuration as described with regard to FIGS. 2*a*-3*b* have the same reference numerals.

The embodiment illustrated FIGS. 4*a*-4*b*, 5*a*-5*b* is for example a PVL occluder. PVL occluders and sick shapes are disclosed in WO 2013/041721A1, of the same applicant as the present application, which is incorporated by reference herein in its entirety for all purposes. The disc(s) and waist portion of the WO 2013/041721A1 PVL device may advantageously be provided with the improvement described herein. The disc 16 or disc 14, however, have concave curved section and a convex curved outer circumference 5, 7 at an opposed axial portion of the disc. This is particularly advantageous when the concave section is in apposition or adjacent an artificial heart valve when implanted. The convex curved opposed circumference is anatomically advantageous in certain target areas to provide an advantageous occlusion of a paravalvular leak while having advantageous retention of the PVL occluder in place.

In still other embodiments, the occluder has a single proximal element, such as for an LAA occluder. The intermediate element may form a lobe, such as a cylindrical body having an end portion formed by the interlaced structure and with a diameter not exceeding the diameter of the intermediate element. The intermediate element or lobe may be stretchable as has been described with regard to FIGS. 2*a*-3*b*. Hooks may be attached to the distal element 6 (if present) and/or the intermediate element 8 and may engage an anatomical structure, such as an LAA. After the hooks engage the vessel wall, intermediate structure may be stretched, and the proximal element positioned outside of the anatomical structure. Due to the stretchability of the intermediate element/lobe, the occluder is more flexible and conforms the shape of the anatomical structure, where in the performance of the occluder is enhanced.

An LAA occluder is for instance disclosed in WO2019197569, of the same applicant as the present application, which is incorporated by reference herein in its entirety for all purposes. The LAA device disclosed in WO2019197569 may advantageously be provided a waist portion and disc(s) with the improvement described in the present disclosure.

In embodiments, the LAA occluder may also have a distal anchoring element alternatively or additionally to the mentioned hooks. Such an LAA occluder is for instance disclosed in U.S. Pat. No. 8,100,938B1, of the same applicant as the present application, which is incorporated by reference herein in its entirety for all purposes. The LAA device disclosed in U.S. Pat. No. 8,100,938B1 may advantageously be provided a waist portion and disc(s) with the improvement described in the present disclosure.

AFR devices allow for a controlled flow across the occlude when implanted, see e.g. WO2016/038115A1, of the same applicant as the present application, which is incorporated by reference herein in its entirety for all purposes. The AFR device disclosed in WO2016/038115A1 may advantageously be provided a waist portion and disc(s) with the improvement described in the present disclosure. The occluder 1 may have a through channel as shown and described in WO2016/038115A1, for instance the through channel 106 in the Figures and description of WO2016/038115A1. The attachment element 11 for attaching the occluder 1 may also be provided off-center from the central axis 10, such as disclosed in WO2016/038115A1, the base body 3 may be provided with a suitable through channel upon heat setting to provide an AFR according to the present disclosure. A double layer disc is for instance shown in FIG. 4c of WO2016/038115A1 and detailed described in the corresponding description. These particular AFR elements are incorporated herein by reference. The first pitch section 3*a* may be part of the inner layer of one or both the double folded discs. This provides for an advantageous occluder 1, here in the example of an AFR device.

The load to extension ratio may be determined using a tensile testing machine, such as the tensile testing machine with device number 10017 and Brand Lloyd Instruments, by AMETEK Sensors, Test & Calibration. The test procedure comprises:

- attach one end of the occluder 1 to a fixed reference and the other end of the occluder 1 to a tensile testing machine.
- extend the waist of the occluder using the tensile testing machine up to 3N with a tensile test speed of 600 mm/min. 3N is chosen as the maximum applied force to demonstrate stretchability of the occluder at low forces.
- Record the amount of extension or elongation of the occluder without the shape of the proximal and/or the distal element being distorted.
- Release the tension applied to the occluder, and observe the reversibility of the stretch behavior, i.e. that the device can return to its original shape without deformation after release of tension.

The below table illustrates test embodiments A and B falling within the above-mentioned ranges of the D1, D2, D3, L1 and L2:

| Test sample | D1 (mm) | D2 (mm) | D3 (mm) | L1 (mm) | L2 (mm) |
|---|---|---|---|---|---|
| Embodiment A | 10 | 4 | 2 | 6 | 10 |
| Embodiment B | 10 | 4 | 2 | 8 | 14 |

The test method was applied to test embodiments A and B defined above and using an Occlutech® mVSD Occluder, size 4, article no. 71VSD04, as reference. The 71VSD04 mVSD occluder is made of a base body with a single pitch. The overall shape of embodiments A and B corresponds to the shape illustrated in FIGS. 2*b* and 3*b*. Hence, embodiments A and B have a proximal element and a distal element shaped as a disc, and an intermediate element in the form of an extendable waist. The disc shape is circular. The mVSD Occluder has an overall similar shape, but has a more uniform and conventional stretchability, i.e. the elasticity of the intermediate element is similar to the stretchability of the proximal element/distal element and is made from a single pitch braid. The diameter of the intermediate element or waist is 4 mm, the diameter of the proximal element and the distal element (discs) is 10 mm, and the height of the waist or intermediate element is 7 mm.

The stretching behavior of the embodiments of the present invention relative the mVSD device is illustrated in the below table:

| Test sample | Initial length of occluder (mm), L1 | Stretched length of occluder (mm), L2 | Force at stretched length L2 (N) | Reversible elongation (mm) (L2-L1) | Elongation (%) |
|---|---|---|---|---|---|
| Embodiment A | 6 | 13.6 | 3 | 7.6 | 127 |
| Embodiment B | 8 | 19.3 | 3 | 11.3 | 141 |
| mVSD Occluder | 7 | 9.2 | 3 | 2.2 | 31 |

The test samples had the same raw material and sterilization method. The pitch of the braid and the heat setting varied between embodiments A and B relative the mVSD Occluder. There are numerous combinations of braid patterns and heat settings that may be applied to achieve the above characteristics, which falls within the disclosure as described above with regard to embodiments of the invention.

As can be seen from the above table, the embodiments of the present invention can be elongated or extended substantially longer than the conventional device. Particularly, the test demonstrates that the occluder according to embodiments of the invention may be stretched or elongated reversible, i.e. without distorting the original shape, such as length or disc diameter, of the device after elongation;

100% to 150% when the applied load is 3 N

50% to 100% when the applied load is 1 N

This should be compared to the regular occluders, exemplified by the mVSD occluder, characterized by being stretched or elongated reversible without distorting the original shape, such as length or disc diameter, of the device after elongation;

0% to 35% when the applied load is 3 N

0% to 30% when the applied load is 1 N

It should also be appreciated that features disclosed in the foregoing description, and/or in the foregoing drawings and/or following claims both separately and in any combination thereof, be material for realizing the present invention in diverse forms thereof. When used in the following claims, the terms “comprise”, “include”, “have” and their conjugates mean, “including but not limited to”.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

The invention claimed is:

1. Occluder, comprising:

a single continuous tubular braided structure made of an integral base body of at least one wire and having a pitch, said pitch varies along an axial length of the base body with one or more pitch transition sections, the one or more pitch transition sections is fixed along the base body; the occluder being heat set to have a post-heat-set shape including:

a post-heat-set proximal retention element having an outer circumference and a distal inner diameter at a first element-transition section in a relaxed state of the occluder, a post-heat-set distal retention element having an outer circumference and a proximal inner diameter at a second element-transition section in the relaxed state of the occluder, and a post-heat-set intermediate element extending between the first and second element-transition sections of the proximal retention element and the distal retention element, wherein the post-heat-set shape transitions integrally along the single continuous tubular braided structure from the proximal retention element to the intermediate element at the first element-transition section, and wherein the post-heat-set shape transitions integrally along the single continuous tubular braided structure from the distal retention element to the intermediate element at the second element-transition section, wherein the post-heat-set shape of the occluder includes post-heat-set aspects where:

said pitch varies from a first pitch to a second pitch at a first pitch transition section of said one or more pitch transition sections, wherein the first pitch transition section is located at a pitch transition post-heat-set location on one of said retention elements as a particular retention element, wherein the pitch transition post-heat-set location is closer to the intermediate element or central axis of said occluder than to the outer circumference of the particular retention element when the occluder is in the relaxed state, the first pitch transition section on the particular retention element is distinct from the respective element-transition section between the intermediate element and the particular retention element, wherein the first pitch transition section is located between the outer circumference and the inner diameter of at least one of the proximal retention element and the distal retention element when the occluder is in the relaxed state, wherein the respective element-transition section variably moves along a post-heat-set longitudinal range of the integral base body while the occluder is extended from the relaxed state to the axially extended state, an axial post-heat-set position of at least one of said first and second element-transition sections is axially variable from a first axial position to a second axial position that is closer to said central axis when the occluder is extended from the relaxed state to the axially extended state, wherein a diameter of said intermediate element is reduced from a relaxed diameter thereof, when the occluder is in the axially extended state; and the outer circumference of the proximal retention element and the outer circumference of the distal retention element remain substantially constant in both the first axial position during the relaxed state and the second axial position during the axially extended state.

2. The occluder according to claim 1, wherein at least one of the proximal retention element and the distal retention element comprises at least the first pitch, and the intermediate element comprises the second pitch only along an axial length of the intermediate element.

3. The occluder according to claim 1, wherein at least one of said outer circumference of said proximal retention element and said distal element is substantially constant when said inner diameter is reduced upon stretching said occluder.

4. The occluder according to claim 1, wherein the proximal retention element and the distal retention element have an identical pitch different from a pitch of said intermediate element.

5. The occluder according to claim 1, wherein the intermediate element comprises a longitudinal section with one pitch and a longitudinal section with another pitch along an axial length of the intermediate element.

6. The occluder according to claim 1, wherein the intermediate element is at least partly straight or waisted in shape relative a longitudinal axis of the occluder when the occluder is in the relaxed state.

7. The occluder according to claim 1, wherein the occluder is a Patent Ductus Arteriosus (PDA) occluder, Paravalvular Leak Device (PLD), transcatheter aortic valve implantation PLD (TAVI-PLD), Ventricular Septal Defect (VSD) occluder, Atrial septal defect (ASD) occluder, Patent Foramen Ovale (PFO) occluder, Left Atrial Appendage (LAA) occluder, interatrial shunt device, Atrial Flow Regulator (AFR) device, fistula device, or vascular plug (VP) device.

8. The occluder according to claim 1, wherein said distal retention element or said proximal retention element is shaped into a disc.

9. The occluder according to claim 8, wherein said disc is double folded in said heat setting and the first pitch transition section is positioned on an inner layer of said disc, respectively.

10. The occluder according to claim 1, wherein the occluder is extendible from the relaxed state to the axially extended state, which is longer in the longitudinal direction of the occluder, than the relaxed state, and wherein the load to extension ratio, measured in N/mm, provided by the occluder is less than about 0.75 when extended at least 2 mm.

11. The occluder according to claim 10, wherein the load to extension ratio, measured in N/mm, provided by the occluder is less than 0.75 N/mm when extended from at least 2 mm and up to about 6 mm.

12. The occluder according to claim 10, wherein a reduction of a cross-sectional diameter of the intermediate element is less than 60% when extended from the relaxed state to an extended state.

13. The occluder according to claim 1, wherein the outer circumference of at least one of the proximal retention element and the distal retention element is substantially constant when the occluder is extended in length more than 50% of the relaxed state and up to about 150% of the relaxed state.

14. Occluder, comprising:

a single continuous tubular braided structure made of an integral base body of at least one wire and having a pitch, said pitch varies along an axial length of the base body with one or more pitch transition sections, the one or more pitch transition sections is fixed along the base body; the occluder being heat set to have a post-heat-set shape including:

a post-heat-set proximal retention element having an outer circumference and a distal inner diameter at a first element-transition section in a relaxed state of the occluder;

a post-heat-set distal retention element having an outer circumference and a proximal inner diameter at a second element-transition section in the relaxed state of the occluder;

a post-heat-set intermediate element extending between the first and second element-transition sections of the proximal retention element and the distal retention element, wherein the post-heat-set shape transitions integrally along the single continuous tubular braided structure from the proximal retention element to the intermediate element at the first element-transition section, and wherein the post-heat-set shape transitions integrally along the single continuous tubular braided structure from the distal retention element to the intermediate element at the second element-transition section, wherein the post-heat-set shape of the occluder includes post-heat-set aspects where:

said pitch varies from a first pitch to a second pitch at a first pitch transition section of said one or more pitch transition sections, wherein the first pitch transition section is located at a fixed pitch transition post-heat-set location on one of said retention elements as a particular retention element, the first pitch transition section on the particular retention element is distinct from the respective element-transition section between the intermediate element and the particular retention element, wherein the pitch transition post-heat-set location is located closer to a center axis or the intermediate element of said occluder than the outer circumference of the particular retention element when the occluder is in the relaxed state, wherein the first pitch transition section is located between the outer circumference and the inner diameter of at least one of the proximal retention element and the distal retention element when the occluder is in the relaxed state, wherein the respective element-transition section variably moves along a post-heat-set longitudinal range of the integral base body while the occluder is extended from the relaxed state to the axially extended state, the occluder is extendible from the relaxed state to the axially extended state, which is longer in the longitudinal direction of the occluder, than the relaxed state, and wherein the post-heat-set load to extension ratio, measured in N/mm, provided by the occluder is less than about 0.75 when extended at least 2 mm, without distortion of the proximal or distal retention elements, and wherein an axial post-heat-set position of at least one of said first and second element- transition sections is axially variable from a first axial position to a second axial position that is closer to a central axis of the occluder, and a diameter of said intermediate element is reduced from a relaxed diameter thereof, when the occluder is extended from the relaxed state to the axially extended state.

15. The occluder according to claim 14, wherein the load to extension ratio, measured in N/mm, provided by the occluder is less than 0.75 N/mm when extended from at least 2 mm and up to about 6 mm.

16. The occluder according to claim 14, wherein a reduction of a cross-sectional diameter of the intermediate element when extended from the relaxed state to an extended state is less than 60%.

17. The occluder according to claim 14, wherein the occluder is a Patent Ductus Arteriosus (PDA) occluder, Paravalvular Leak Device (PLD), transcatheter aortic valve implantation PLD (TAVI-PLD), Ventricular Septal Defect (VSD) occluder, Atrial septal defect (ASD) occluder, Patent Foramen Ovale (PFO) occluder, Left Atrial Appendage (LAA) occluder, interatrial shunt device, Atrial Flow Regulator (AFR) device, fistula device, or vascular plug (VP) device.

18. The occluder according to claim 14, wherein the distal retention element and/or the intermediate element comprises hooks.

19. The occluder according to claim 14, wherein the outer circumference of at least one of the proximal retention element and the distal retention element is substantially constant when the occluder is extended in length more than 50% of the relaxed state and up to about 150% of the relaxed state.

20. A method of manufacturing an occluder, the method comprising:

forming an integral base body of at least one wire providing a single continuous tubular braided interlaced structure having a pitch, said pitch varies along an axial length of the occluder base body with one or more pitch transition sections, the one or more pitch transition sections is fixed along the base body;

heat setting the base body to have a post-heat-set shape including:

a post-heat-set proximal retention element having an outer circumference and a distal inner diameter at a first element-transition section in a relaxed state of the occluder, a post-heat-set distal retention element having an outer circumference and a proximal inner diameter at a second element-transition section in the relaxed state of the occluder, and a post-heat-set intermediate element extending between the first and second element-transition sections of the proximal retention element and the distal retention element, wherein the post-heat-set shape transitions integrally along the single continuous tubular braided structure from the proximal retention element to the intermediate element at the first element-transition section, and wherein the post-heat-set shape transitions integrally along the single continuous tubular braided structure from the distal retention element to the intermediate element at the second element-transition section, wherein the post-heat-set shape of the occluder includes post-heat-set aspects where:

said pitch varies from a first pitch to a second pitch at a first pitch transition section of said one or more pitch transition sections, wherein the first pitch transition section is located at a pitch transition post-heat-set location on one of said retention elements as a particular retention element, the first pitch transition section on the particular retention element is distinct from the respective element-transition section between the intermediate element and the particular retention element, wherein the respective element-transition section variably moves along a post-heat-set longitudinal range of the integral base body while the occluder is extended from the relaxed state to the axially extended state, the pitch transition post-heat-set location is closer to the intermediate element or central axis of said occluder than to the outer circumference of the particular retention element when the occluder is in the relaxed state, or wherein the occluder is extendible from the relaxed state to the axially extended state, which is longer in the longitudinal direction of the occluder, than the relaxed state, and wherein the post-heat-set load to extension ratio, measured in N/mm, provided by the occluder is less than about 0.75 when extended at least 2 mm, without distortion of the proximal or distal retention elements, the first pitch transition section is located between the outer circumference and the inner diameter of at least one of the proximal retention element and the distal retention element when the occluder is in the relaxed state, and wherein an axial post-heat-set position of at least one of said first and second element- transition sections is axially variable from a first axial position to a second axial position that is closer to said central axis when the occluder is extended from the relaxed state to the axially extended state and a diameter of said intermediate element is reduced from a relaxed diameter thereof when the occluder is in the axially extended state.

* * * * *